United States Patent [19]

Spaziante et al.

[11] 4,201,647
[45] May 6, 1980

[54] MEASURING ELECTRODES AND PROCESS

[75] Inventors: Placido M. Spaziante, Lugano, Switzerland; Luigi Giuffre; Giovanni Modica, both of Milan, Italy

[73] Assignee: Panclor S.A., Taverne, Switzerland

[21] Appl. No.: 908,262

[22] Filed: May 22, 1978

[30] Foreign Application Priority Data

Jun. 8, 1977 [CH] Switzerland ............... 7089/77

[51] Int. Cl.² ............... G01N 27/30; G01N 27/46
[52] U.S. Cl. ............... 204/195 F; 204/1 T; 204/195 M; 204/195 R; 204/294; 429/91
[58] Field of Search ............... 204/1 T, 195 M, 195 F, 204/195 R, 294; 429/91

[56] References Cited

U.S. PATENT DOCUMENTS

| 3,528,778 | 9/1970 | McKaveney et al. | 204/195 M X |
| 3,814,699 | 6/1974 | Baldieri et al. | 204/294 X |
| 3,824,453 | 7/1974 | Baker | 204/1 T X |
| 3,826,971 | 7/1974 | Jasinski et al. | 204/195 M X |
| 3,856,574 | 12/1974 | Amagi et al. | 204/294 X |
| 3,881,039 | 4/1975 | Baldieri et al. | 204/294 X |
| 3,926,764 | 12/1975 | Ruzicka et al. | 204/195 F |
| 4,120,774 | 10/1978 | Hart | 204/294 |
| 4,126,735 | 11/1978 | Fritts | 429/91 |

Primary Examiner—Arthur C. Prescott
Attorney, Agent, or Firm—Hammond, Littell, Weissenberger & Muserlian

[57] ABSTRACT

A novel measuring electrode for determination of the concentration of anionic species in aqueous solutions by measuring the potential difference between the measuring electrode and a reference electrode comprising a body provided with an outer surface comprised of graphite or carbon black dispersed in a chemically inert matrix, said electrode being preactivated by anodic polarization in an aqueous alkaline or acid solution, the process of activating the said electrode and a method of ascertaining the charge state of an electric accumulator by determining the strength of the electrolyte therein.

13 Claims, 7 Drawing Figures

MEASURING ELECTRODES AND PROCESS

STATE OF THE ART

Determination of the concentration of an acid or a base can be effected either directly or indirectly. The indirect method consists essentially of volumetric, potentiometric, conductometric and, wherever possible, of weight titrations which are the most used methods for an indirect determination of the strength thereof. These methods are reliable but disadvantageous when an immediate determination of the strength of an acidic or a basic solution is needed and they involve the loss of the sample of the solution. Furthermore, these indirect methods can be applied only in dilute solutions and when a strength determination of a concentrated solution is required, sampling and dilution of the sample must be effected.

The direct methods, i.e. instant determination, of determining the strength of an acid or a base consists in the measurement of some physical properties of the solution and particularly the electrical conductivity, the density or the potential exhibited by an indicator or measuring electrode sensitive to the ionic species whose concentration has to be determined connected to a reference electrode with a known constant potential, that is the setting up of a galvanic cell wherein the open circuit potential is proportional to the concentration of the relevant ionic species. For some applications, substances whose color changes according to the solution pH are employed for a colorimetric determination of the strength.

The methods other than the colorimetric method have the advantage that they do not alter the solution but they are not of common use. Conductimetric strength determinations are reliable only in the case of solutions constituted by a single electrolyte. The method cannot be applied to solutions comprising more than one electrolyte wherein all the ionic species would contribute to the measured conductivity value. The use of the density meters is limited for the same reasons. The potentiometric method utilizing measuring electrodes selectively sensitive to the particular ionic species overcomes the disadvantages of the other methods.

Therefore, there is a need for highly selective measuring electrodes which are sensitive over a large range of concentrations. At present, an acid strength potentiometric determination is carried out with electrodes sensitive to the $H_3O^+$ cation, for example by quinone glass electrodes. However, these electrodes can be utilized only with dilute acid solutions where the mobility of all the other ions present is much lower than the $H_3O^+$ cation $$H_3O^+ Mo^+ = 346 Ohm^{-1} cm^2 eq^{-1}$$

In case of acids with concentrations higher than 1 N, the $H_3O^+$ is no longer the most mobile species and the commonly used electrode, that is to say, the glass electrode, assumes a practically constant potential and becomes insensitive to the variations of the concentration.

To determine the concentration of an acid or a base over a large concentration range, the measuring electrode must be reversibly sensitive to the more unstable species present in the system and must be chemically resistant for a long period of time to the acid or basic environment. Particularly, it is of great practical interest to determine sulfuric acid concentrations instantaneously and continuously in the range of concentrations from 10 to 30% which is the range of concentration found in lead acid batteries used for the reversible storage of energy.

Considering the discharging voltage characteristics of a lead battery, it is evident that the voltage determination cannot give a reliable indication of the charge condition of the battery since even near full discharge the voltage is almost the same as that of a fully charged battery. A reliable method to assess the charge condition is to measure the acid concentration. Results of conductivity determinations are not reliable due to the presence of impurities and the density determination while reliable entails a bothersome manual inspection and is not easily automatied. Therefore, the determination of the state of charge of a lead-acid battery can be effected potentiometrically by a measuring electrode sensitive to the anion at least up to acid concentrations of 30% to 40%.

In the case of sulfuric acid solutions, the sulfuric acid contained in the solution dissociates according to the following equations:

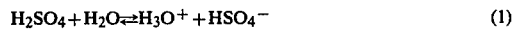

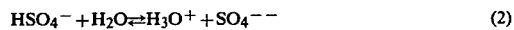

with the concentration of the anions $HSO_4^-$ and $SO_4^{--}$ depending on the acid concentration. In sulfuric acid concentrations from 10 to 80%, practically only the ions coming from reaction 1 are present in the solution and it has been ascertained that in this concentration range, the most mobile species is the anion $HSO_4^{--}$ which is 2 to 3 times more mobile than the proton. Practically, the determination of the strength of the sulfuric acid in this concentration range is limited to the determination of the anion $HSO_4^-$.

OBJECTS OF THE INVENTION

It is an object of the invention to provide a novel measuring electrode for determining the concentration of anionic species in an acid or basic solution even at high concentrations.

It is a further object of the invention to provide a method for the instantaneous determination of the charge condition of a lead-acid battery.

These and other objects and advantages of the invention will become obvious from the following detailed description.

THE INVENTION

The novel measuring electrode of the invention is comprised of a body provided with an outer surface comprised of graphite or carbon black dispersed in a chemically inert matrix, said electrode being preactivated by chemical or electrochemical treatment before use.

It has unexpectedly been found that graphite or carbon black chemically or electrochemically activated in an acid or alkaline solution are exceptionally sensitive to the variation of anion concentrations. It is well known that carbon exhibits various allotropic stages and in particular, as graphite, it crystallizes in layers wherein every carbon atom is bonded to three other atoms presenting on the whole an hexagonal structure. The carbon-carbon bond has a shorter length than the simple bond (1.415 Å) and the presence of partial double bonds must be assumed. The crystallization layers of the carbon atoms are arranged 3.35 Å apart and are bonded by residual valence, or Van der Waal, forces. A slightly different crystallization form is represented by carbon black which is constituted of groups of carbon atoms arranged like graphite in parallel layers set in couples and disoriented at an average distance of 3.7 Å. Therefore, carbon black compared with graphite presents a more disordered lattice characteristic.

The lamellar structure of these substances allows the infiltration of various organic and inorganic species which may cause a structure swelling due to the increase of the interplanar distances. Some interlamellar compounds may form spontaneously, such as those comprising alkali metals or halides and oxides of transition metals and other compounds may be formed by chemical or electrochemical means.

Of great interest are the compounds obtained by anodic polarization of graphite in acids or bases and in particular in acids such as nitric acid, sulfuric acid, phosphoric acid, hydrochloric acid, hydrobromic acid, hydroiodic acid, hydrofluoric acid, $HClO_4$, acetic acid, chloroacetic acid or oxalic acid and bases such as sodium hydroxide, potassium hydroxide and lithium hydroxide.

For example, during the anodic polarization of graphite in concentrated $H_2SO_4$, the introduction of one bisulfate anion ($HSO_4^-$) and two $H_2SO_4$ molecules takes place at every 24 atoms of carbon giving rise to the formation of the compound:

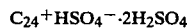
$$C_{24}^+ HSO_4^- \cdot 2H_2SO_4$$

Similar compounds are obtained by anodic polarization of graphite in the other mentioned bases and acids with the consequent formation of the compounds with the formula

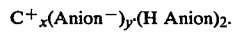
$$C^+_x(Anion^-)_y \cdot (H\ Anion)_2.$$

Several theories have been put forward on the formation of these compounds and the most common one admits the formation of the species $C_x^+$, that is the formation of a stabilized carbocation on x carbon atoms. Therefore it is presumed that in the graphite and carbon black substrates of the electrodes of the invention, positive charges are present after the activating process. These cations are arranged in a macrostructure with practically nil transfer number and may be screened by the anionic cloud without giving rise to a counter-screening with respect to the anion species.

Since graphite tends to flake off when subjected to anodic polarization in sulfuric acid and other strongly oxidizing solutions, it is also a object of the present invention to provide graphite or carbon black measuring electrodes which are sufficiently stable during both the activation process and during prolonged operation. The measuring electrode is therefore constituted of carbon in the form of graphite or carbon black powders set in a chemically inert matrix, said electrode being preferably preactivated by anodic polarization in an acid or alkaline solution. The electrode is preferably of a uniform composition but may also be comprised of an electrically conductive base provided with an outer coating of the said aggregate.

The chemically inert matrix is a resin and examples of useful resins are theromplastic polymers such as polyethylene thermosetting polymers such as epoxides, polyester, phenolic resins, furan resins, etc. or inorganic polymers such as silicones, polysilicates etc.

The carbon-resin aggregates must have a sufficient electrical conductivity for operating satisfactorily as measuring electrodes and are prepared by mixing graphite or carbon black powders with the powdered resin to form a mixture containing 30 to 95% by weight of the powdered carbon. The preparation of these aggregates is conveniently effected by well known plastic material technologies such as: extrusion, pressing and-/or sintering.

The preferred process of the invention for preactivating the electrodes comprises subjecting the electrode of the invention to anodic polarization with a counter-electrode in an aqueous alkaline or acid solution for at least 5 seconds at a current density of 0.001 to 2.0 $A/cm^2$. The anodic polarization is most preferably effected in sulfuric acid of 5 to 98% concentrations for a time greater than 10 seconds.

As the counter-electrode, any suitable material resistant to the cathodic conditions can be utilized and preferably platinum group metals, graphite, titanium, or lead counter-electrodes have been satisfactorily utilized. In particular, it has been noted that the activating conditions such as acid concentration, temperature and activation time do not affect the measuring properties of the activated electrode beyond certain minimum anodization conditions which vary obviously from the acid or basic solution employed, and consequently the said parameters may vary within large limits.

The electrodes thus activated have been successfully utilized for potentiometric determinations of the strength of concentrated acidic or basic solutions using as the reference electrode systems commonly used for the particular type of solution being tested such as the saturated calomel reference electrode, the mercurous sulfate/$K_2SO_4$ electrode, the mercurous sulfate/$H_2SO_4$ electrode, etc.

The measuring electrode of the invention is highly sensitive to concentration variations with its sensitivity in the range of 200 to 300 millivolt for a concentration variation of 10%. The electrode of the invention does not substantially exhibit hysteresis phenomena and therefore it can be utilized for plotting the concentration of solutions either during increasing concentration or during the decreasing step without any other expedient.

The electrodes of the invention may partially loose their initial sensitivity after prolonged use. However, it has been proved that their sensitivity can be restored to the original one by repeating the activating process for a brief period. The measuring electrode of the invention may be activated indifferently through anodic polarization either in acid or in basic solutions and it results in sensitivity to the variation of anion concentration either in acidic or in basic solutions independant of the activating conditions.

According to a preferred embodiment of the invention, the electrode is utilized for determining the charge conditions of a battery of widespread use such as the lead-acid storage battery in which the measuring electrode is constituted by an activated electrically conductive resin and graphite (or carbon black) electrode and a reference electrode suitable for measurement in sulfuric acid which are immersed in the electrolyte contained in the battery with or without a third electrode acting as counter-electrode (cathode) for the activation of the measuring electrode.

The measuring electrode, through a suitable control circuit illustrated hereafter operable by a push button or a toggle switch, is anodically polarized with respect to the cathode of the battery itself or to a counter-electrode made of graphite or other suitable cathodic material connected to the cathode of the battery for a time varying from 10 to 60 seconds. This time is pre-set by use of a time-delay switch included in the control circuit and this stage is intended to restore the normal activity of the measuring electrode in case it becomes inactive after a long period of time. After the above step, the timing means automatically commutes the measuring electrode in the measurement circuit comprising a duly calibrated indicator, which, driven by the voltage between the measuring electrode and the reference electrode, indicates the state of charge of the battery, preferably in percent of charge.

In another embodiment of the invention, the measuring electrode is constantly subjected to a minimum anodic polarization with respect to a counter-electrode connected to the battery cathode during periods of inactivity to keep it always in a fully active state. When a reading switch is actuated, the measuring electrode is instantaneously commutated in the measurement cirucit. Obviously, in this case, the anodic current impressed on the measuring electrode must be limited by a suitable circuit to prevent damage to the measuring electrode through an excessive anodization which may cause the consumption and flaking off of the carbon. Furthermore, the counter-electrode must be automatically commutated onto one of the other electrodes of the battery during the charging of the battery when the polarity is reversed.

Practically, with the electrode of the invention, a variation of 270–300 mV has been recorded which corresponds to the condition of full charge and complete discharge of the battery and this remarkable potential difference which is substantially linear with respect to the electrolyte concentration variation permits an exact and immediate indication of the state of charge of the battery.

Referring now to the drawings.

Figure 1:
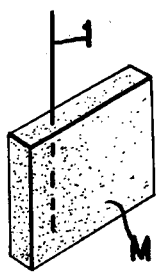
FIG. 1 illustrates a measuring electrode of the invention in the form of a small solid bar and FIG. 2 illustrates a measuring electrode of the invention having a cylindrical form.
Figure 2:

In FIGS. 1 and 2, the measuring electrode of the invention is indicated as M in both figures and can be shaped as a small bar as in FIG. 1, or as a rod as in FIG. 2, or in any other convenient shape. The measuring electrode consists of an aggregate of graphite or carbon black powders and a chemically inert material, and as indicated in FIGS. 1 and 2, can be provided with a lead-in 1 of conductive material which is set inside the bulk of the electrode during the molding step or connected by threading or cementing with electrically conductive cements.

Figure 3:
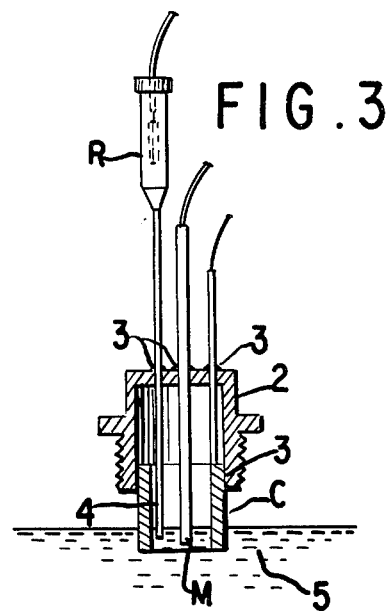
FIG. 3 is a cross-sectional view of a typical assembly consisting of a measuring electrode of the invention with a reference electrode and a counter-electrode for the activation process.

In FIG. 3, the assembly is comprised of a measuring electrode M, a counter-electrode C for activating the measuring electrode M by anodic polarization of the same in an acidic or basic solution and a reference electrode R. The three electrode assembly is opportunely set into a threaded cap 2 made of inert and electrically non-conductive material by cementation with a chemically resistant adhesive such as an epoxy or phenolic resin 3. The glass capillary 4 of the reference electrode, the measuring electrode M and the counter-electrode C are immersed up to a certain depth in electrolyte 5 when the cover is fixed onto the container.

Figure 4:
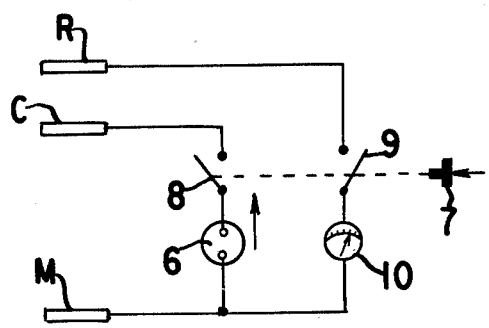
FIG. 4 is a schematic electrical circuit allowing the preventive polarization of the measuring electrode and subsequent measurement of the electrolyte concentration.

FIG. 4 is a simplified scheme of an electric circuit of the invention allowing for preventive polarization of the measuring electrode M and subsequently for measuring the potential difference between the measuring electrode M and the reference electrode R. According to the illustrated circuit, the measuring electrode M continuously undergoes a certain anodic polarization impressed by current generator 6 with respect to the counter-electrode C. When the concentration of the electrolyte in which the electrodes are immersed has to be determined, reading button 7 is pressed. This opens switch 8 and simultaneously closes switch 9 whereby it is possible to read the electrolyte concentration on instrument 10, duly calibrated to indicate the concentration percentage based on the potential difference between measuring electrode M and reference electrode R. Releasing the reading button 7, switch 9 opens and switch 8 closes again and the measuring electrode M is again anodically polarized with respect to the counter-electrode C.

Figure 5:
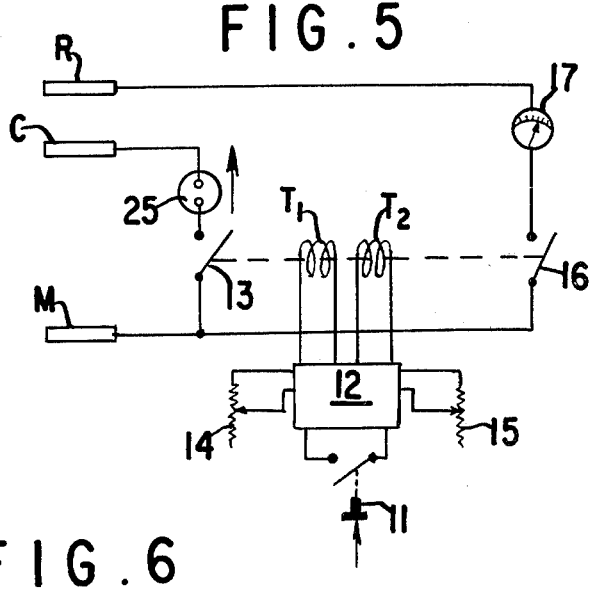
FIG. 5 is a schematic electrical circuit particularly useful for the quick ascertainment of the state of charge of a battery.

FIG. 5 is a diagram of another electrical circuit of the invention which circuit is particularly suitable for implementing a quick remote reading system of the state of charge of a battery. The three electrodes, measuring electrode M, reference R and counter-electrode C, are permanently immersed in the electrolyte of the battery and activating reading button 11 activates double timing means 12 which in turn activates relay T1 closing switch 13. This anodically polarizes measuring electrode M with respect to the counter-electrode C for a pre-set period of time varying from some seconds to some minutes, said time relay being preset by calibration rheostat 14. Current generator 25 may be an auxiliary battery or the same battery whose state of charge has to be determined and when the pre-set time is over, double timing means 12 disengages relay T1 thereby opening switch 13 and, simultaneously, activating relay T2 closing switch 16. Therefore, on a suitably calibrated scale of instrument 17, the state of charge of the battery will be indicated in percentage based on the detected voltage between the measuring electrode M and the reference electrode R. After a prefixed period of time pre-set by suitably calibrating rheostat 15, the timing means disengages relay T2 and therefore switch 16 closes and the system remains inactive until the reading button is pushed again.

Figure 6:
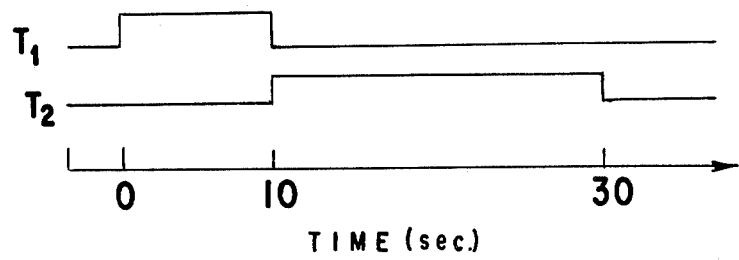
FIG. 6 illustrates the time sequence diagram of the timing means utilized in the circuit of FIG. 5.

In FIG. 6, the time sequence generated by the double timing means 12 of FIG. 5 is illustrated. In the case shown, the first relay T1 is activated for 10 seconds and then relay T2 is activated for 20 seconds. The indicator 10 of FIGS. 4 and 17 of FIG. 5 may be any instrument capable of measuring potential difference in mV with insignificant current absorption such as a potentiometer or a voltmeter. It has been found that a common voltmeter having a high internal resistance may be advantageously used instead of a potentiometer.

Figure 7:
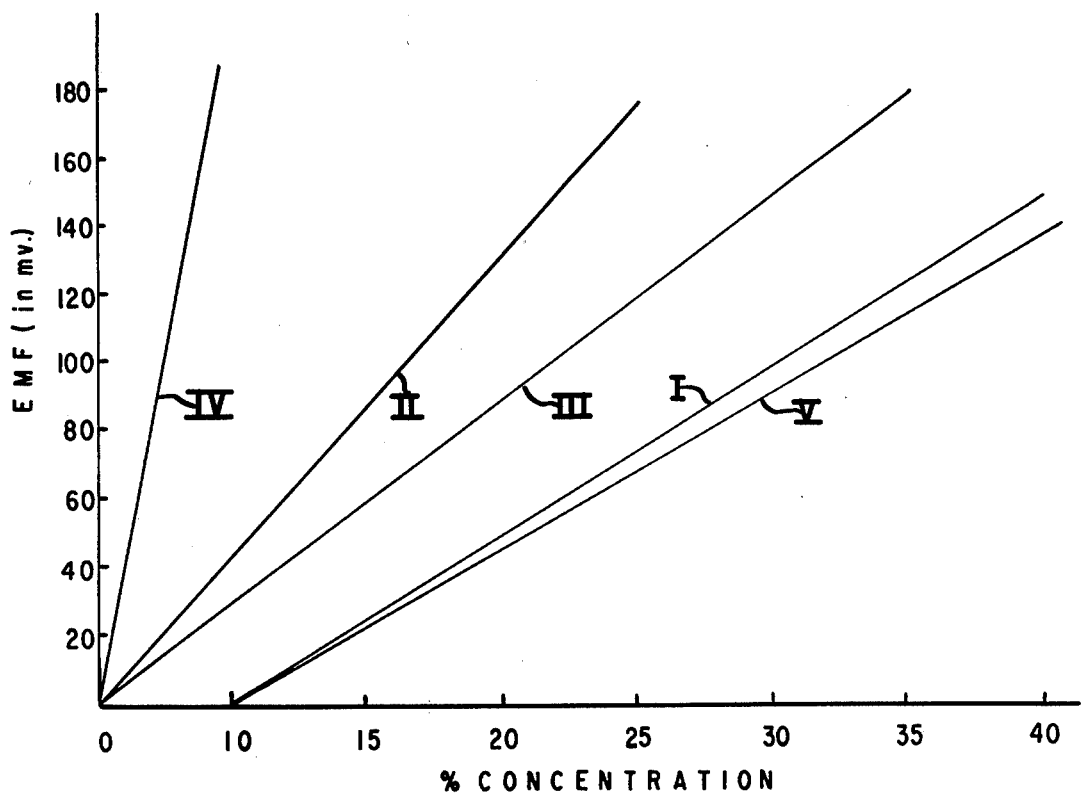
FIG. 7 is a graph of typical plots obtained with reference electrodes of the examples in various electrolytes.

FIG. 7 shows some typical potential plots obtained with measuring electrodes of the invention in various solutions as per the following examples. The concentration is percentage by weight is shown in abscissa and the potential in mV recorded between the measuring electrode and the reference electrode is shown in ordinate.

In the following examples there are described several preferred embodiments to illustrate the invention. However, it is to be understood that the invention is not intended to be limited to the specific embodiments.

EXAMPLE 1

4 g of graphite and 6 g of powdered polyethylene were homogenized in a ball mill and the mixture was extruded in the form of small cylinders of the mixture. A sample cylinder was electrolyzed in a 10% aqueous sulfuric acid solution for 5 minutes at 20° C. with a graphite bar serving as the counter-electrode and the voltage on the electrodes was 3.5 volts. This activated sample electrode was utilized as a measuring electrode by connecting it to a potentiograph Metrohm model E 536 using as the reference electrode, the $Hg/Hg_2SO_4/H_2SO_4$ (80) electrode. An automatic buret Metrohm model E 535 has been used for linearly varying the concentration of a $H_2SO_4$ solution from 10 to 40%. The corresponding potential plot is shown as line I in FIG. 7.

EXAMPLE 2

Using the procedure of Example 1, 7 electrodes were prepared with varying amounts of graphite and polyethylene powder and were activated under the conditions of Table I. A titanium bar was employed as the counter-electrode.

TABLE I

| Sample No. | Graphite Powder grams | Polythene Powder grams | $H_2SO_4$ Conc. % | Temp. °C. | p.d. V | Polariz. Time in Seconds |
|---|---|---|---|---|---|---|
| 1 | 7.0 | 3.0 | 10 | 25 | 3.5 | 60 |
| 2 | 7.0 | 3.0 | 30 | 25 | 3.5 | 60 |
| 3 | 7.0 | 3.0 | 30 | 25 | 3.5 | 30 |
| 4 | 5.0 | 5.0 | 10 | 15 | 3.5 | 60 |
| 5 | 5.0 | 5.0 | 30 | 15 | 3.5 | 60 |
| 6 | 5.0 | 5.0 | 30 | 15 | 3.5 | 30 |
| 7 | 5.0 | 5.0 | 80 | 15 | 3.5 | 30 |

As in Example 1, the treated sample electrodes were used for recording the variation of potential between the sample electrodes and the reference electrode corresponding to a variation from 10% to 30% of the concentration of sulfuric acid solutions. The potential plots, relative to the various samples of Table I, did not show substantial deviations and the maximum deviation of the recorded potential plots was of the order of 3 mV which is less than 1.5%. The concentration of the sulfuric acid solution was varied continuously from 30 to 10% and the same samples were used for recording the potential difference between the sample electrode and the reference electrode. The potential plots recorded for each sample substantially coincides with the potential plot obtained during the inverse cycle, that is to vary the concentration of the sulfuric acid solution from 10% to 30%.

EXAMPLE 3

5 g of powdered Halar resin and 5 g of powdered graphite were throughly mixed and the mixture was formed into small plates about 2 mm thick which were sintered at 200° C. The sample electrode plates were activated by anodic polarization in 20% hydrofluoric acid with a voltage of 3.5 between the sample electrode and the lead counter-electrode for a variable time of 5 to 600 seconds.

The activated electrodes were used with a saturated calomel reference electrode to record a 15 to 25% variation in the concentration of a hydrofluoric acid solution. The sample electrodes which had been activated for a time greater than 10 seconds gave a substantially uniform potential plot and showed a potential variation of 230 mV from a concentration of 5% to 35% and vice versa. The typical potential plot of the various samples is represented by the line II of FIG. 7. Moreover, it has been found that the samples which had been anodized for a time less than 7 seconds gave erratic potential plots and were in no way comparable with the potential plot obtained by the other samples.

EXAMPLE 4

5.0 g of powdered graphite and 4 g of powdered polytetrafluoroethylene were throughly mixed and the mixture was formed into plates which were sintered at 300° C. and then heated at 380° C. for 15 minutes. The samples electrodes were activated in a solution of 20% hydrochloric acid by impressing an anodic potential with a lead counter-electrode and an impressed voltage of 3.5 volts for times varying from 5 to 600 seconds.

The activated electrodes were used for recording a 5 to 35% variation of the concentration of hydrochloric acid and vice versa with the reference electrode used for the determination being a $Hg/Hg_2SO_4/K_2SO_4$ electrode.

EXAMPLE 5

10 g of powdered graphite and 3 g of powdered epoxy resin were throughly mixed and the mixture was formed into small rods with a 3 mm diameter. The samples were activated by anodic polarization in 10% aqueous NaOH for times varing from 5 seconds to 10 minutes while using a variable current density from 0.001 to 1 Amp./cm$^2$. As the counter-electrode, a small graphite rod was utilized.

The treated electrodes were used as measuring electrodes for recording from 5 to 10% variation of concentration of an aqueous sodium hydroxide solution using as the reference electrode, a saturated calomel electrode. The typical potential plot obtained is represented as line IV in FIG. 7.

EXAMPLE 6

10 g of powdered graphite and 4 g of a powdered phenolic resin were throughly mixed and the mixture was formed into small rods with a 3 mm diameter. The sample electrodes were activated by anodic polarization in 10% KOH solution for times varing from 5 seconds to 10 minutes with a variable current density from 0.001 to 1 Amp./cm$^2$, utilizing a graphite rod as counter-electrode.

The treated sample electrodes were used as measuring electrodes for recording the variation of 10 to 40% concentration of an aqueous sulfuric acid solution utilizing as a reference electrode, a saturated calomel electrode. The typical potential plot obtained is recorded as line V in FIG. 7.

EXAMPLE 7

An electrode of Example 1 was formed in the shape of a cylindrical rod with a 3 mm diameter and was assembled together with a saturated calomel electrode inside a cylindrical lead counter-electrode. The 3 electrodes were secured in a polyvinyl chloride threaded cap adapted to the filling hole of a lead-acid battery so that the electrodes would extend into the electrolyte to a depth of 4 mm. The electrodes were electrically connected into the circuit described in FIG. 5 with the time sequence corresponding to that of FIG. 6. The voltage for the anodic polarization of the measuring electrode was taken from the battery being tested and a voltmeter with an internal resistance of 100 kohm/v was used as the indicator.

The battery was discharged gradually over 24 hours and every hour, a push button was actuated to produce the following sequence:
(a) anodic polarization of the measuring electrode with respect to a lead counter-electrode with an impressed voltage of about 3.5 V for a duration of 10 seconds
(b) opening of the anodic polarization circuit
(c) closing of the measuring circuit and recording of the potential difference between the measuring electrode and the reference electrode shown on the voltmeter scale
(d) opening of the circuit of measurement after 30 seconds.

At every hourly measurement, the concentration of the sulfuric acid in the electrolyte of the battery was determined by sampling the electrolyte and determining the sulfuric acid concentration by chemical means. The concentration of the electrolyte at each measurement was reported on the graduated scale of the voltmeter. Eventually, the new graduated scale of the voltmeter shows directly the concentration of the electrolyte in percent, that is the state of charge of the battery in percent. After reaching complete exhaustion of the battery, the potential difference between the measuring electrode and the reference electrode was 270 mV.

The measuring assembly constituted by the three electrodes placed in the electrolyte of the battery is moreover useful in detecting and eventually signalling the lowering of the level of the electrolyte below the recommended minimum. In fact, when the push button is actuated, if the electrodes are not deep enough in the electrolyte, it is possible by means of a simple circuit to actuate a light or sound signal thereby warning the operator that it is necessary to replenish the lowered level of the electrolyte by adding water to the battery before repeating the procedure for determining the state of charge of the battery itself.

The measuring electrodes of the present invention have various advantages over the known electrodes. First, the measuring electrode of the invention is solid and not easily damaged by handling. It has a very high sensitivity to the variation of concentrations even at relatively high concentration levels and it is easily reactivated and it can easily be miniaturized for use in measuring systems applied to batteries, for example, on electric trucks.

Various modifications of the electrodes and processes of the invention may be made without departing from the spirit or scope thereof and it should be understood that the invention is to be limited only as defined in the appended claims.

We claim:
1. A measuring electrode comprised of a body provided with an outer surface comprised of graphite or carbon black dispersed in a chemically inert matrix, said electrode being preactivated by anodic polarization in an aqueous acidic or basic solution.
2. The measuring electrode of claim 1 wherein the inert matrix is an organic resin.
3. The measuring electrode of claim 1 wherein the inert matrix is a thermosetting resin.
4. The measuring electrode of claim 1 wherein the inert matrix is a thermoplastic resin.
5. The measuring electrode of claim 1 wherein the resin is 70 to 5% by weight of the electrode.
6. A measuring apparatus for determining the charged state of a lead-acid battery comprising a measuring electrode of claim 1, a counter-electrode for activating the measuring electrode by anodic polarization and a reference electrode for a lead-acid battery secured in an inert, electrically non-conductive holding means, the said electrodes extending from the holding means a sufficient distance for immersion into a lead-acid battery.
7. The apparatus of claim 6 wherein the inert matrix is an organic resin.
8. The apparatus of claim 6 wherein the inert matrix is a thermosetting resin.
9. The apparatus of claim 6 wherein the inert matrix is a thermoplastic resin.
10. The apparatus of claim 6 wherein the resin is 70 to 5% by weight of the electrode.
11. An apparatus for measuring potential difference to determine the degree of charge of a battery comprising a measuring electrode of claim 1 and a counter-electrode for immersion in the electrolyte of a battery, means for impressing an anodic polarization on the measuring electrode, switching means for interrupting the anodic polarization and for connecting the measuring electrode and the counter-electrode and means for reading the percent of concentration of the electrolyte by the potential difference between the two electrodes.
12. The apparatus of claim 11 wherein the measuring electrode has a matrix of an organic resin comprising 70 to 5% by weight of the electrode and the preactivation is effected by anodic polarization in an aqueous acidic or basic solution.
13. An apparatus for quick determination of the charge of a lead-acid battery comprising a measuring electrode of claim 1, a counter-electrode and a reference electrode all to be immersed in the battery electrolyte means for anodically polarizing the measuring electrode with respect to the counter-electrode, a double timing means for switching the anodic polarization means on and then off for a predetermined time period and means for recording the potential difference between the measuring electrode and the reference electrode to determine the degree of charge of the battery.

* * * * *